US00PP19687P2

(12) United States Plant Patent
Hambali

(10) Patent No.: US PP19,687 P2
(45) Date of Patent: Feb. 10, 2009

(54) ***AGLAONEMA* PLANT NAMED 'TWYAG0021'**

(50) Latin Name: *Aglaonema commutatum* var. *tricolor×A. rotundum hybrida*
Varietal Denomination: TWYAG0021

(75) Inventor: Gregori Garnadi Hambali, Bogor (ID)

(73) Assignee: Kerry's Bromeliad Nursery, Inc., Apopka, FL (US)

( * ) Notice: Subject to any disclaimer, the term of this patent is extended or adjusted under 35 U.S.C. 154(b) by 0 days.

(21) Appl. No.: 11/906,908

(22) Filed: Oct. 4, 2007

(51) Int. Cl.
*A01H 5/00* (2006.01)

(52) U.S. Cl. ..... Plt./376
(58) Field of Classification Search ..... Plt./376
See application file for complete search history.

*Primary Examiner*—Annette H Para
*Assistant Examiner*—S. B McCormick Ewoldt
(74) *Attorney, Agent, or Firm*—Jondle & Associates, P.C.

(57) ABSTRACT

A new *Aglaonema* plant particularly distinguished by very dense leafy, compact and upright and highly branched growth habit, small to intermediate in stature, colorful leaves with distinct pinkish-white and green contrast, profuse suckering, very vigorous growth habit and produces numerous axillary branches and leaves, is disclosed.

2 Drawing Sheets

Genus and species: *Aglaonema commutatum* var. *tricolor×A. rotundum hybrida.*
Variety denomination: 'TWYAG0021'.

BACKGROUND OF THE NEW PLANT

The present invention comprises a new and distinct cultivar of *Aglaonema*, botanically known as *Aglaonema commutatum* var. *tricolor×A. rotundum hybrida,* and hereinafter referred to by the cultivar name 'TWYAG0021'. The new cultivar originated from a hybridization made in 2000 in Bogor, Indonesia. The female parent was an unknown individual plant of *A. commutatum* var. *tricolor* (patent status unknown), while the male parent was an unknown individual plant of *A. rotundum* (patent status unknown). A single plant was chosen in August 2002 for subsequent asexual reproduction.

The new cultivar was created in Bogor, Indonesia and has been asexually reproduced repeatedly by vegetative cuttings and sucker division in Apopka, Fla. and Bogor, Indonesia over a 5-year period. The present invention has been found to retain its distinctive characteristics through successive asexual propagations.

SUMMARY OF THE INVENTION

The following are the most outstanding and distinguishing characteristics of this new cultivar when grown under normal horticultural practices in Apopka, Fla. and Bogor, Indonesia.

1. Small to intermediate in stature;
2. Very densely leafy, compact and upright and highly branched growth habit;
3. Colorful leaves with distinct pinkish-white and green contrast;
4. Profuse suckering;
5. Very vigorous growth habit; and
6. Produces numerous axillary branches and leaves.

DESCRIPTION OF THE PHOTOGRAPHS

This new *Aglaonema* plant is illustrated by the accompanying photographs which show overall plant habit. The colors shown are as true as can be reasonably obtained by conventional photographic procedures. The photographs are of a 16-month old plant.

DESCRIPTION OF THE NEW CULTIVAR

Figure 1:
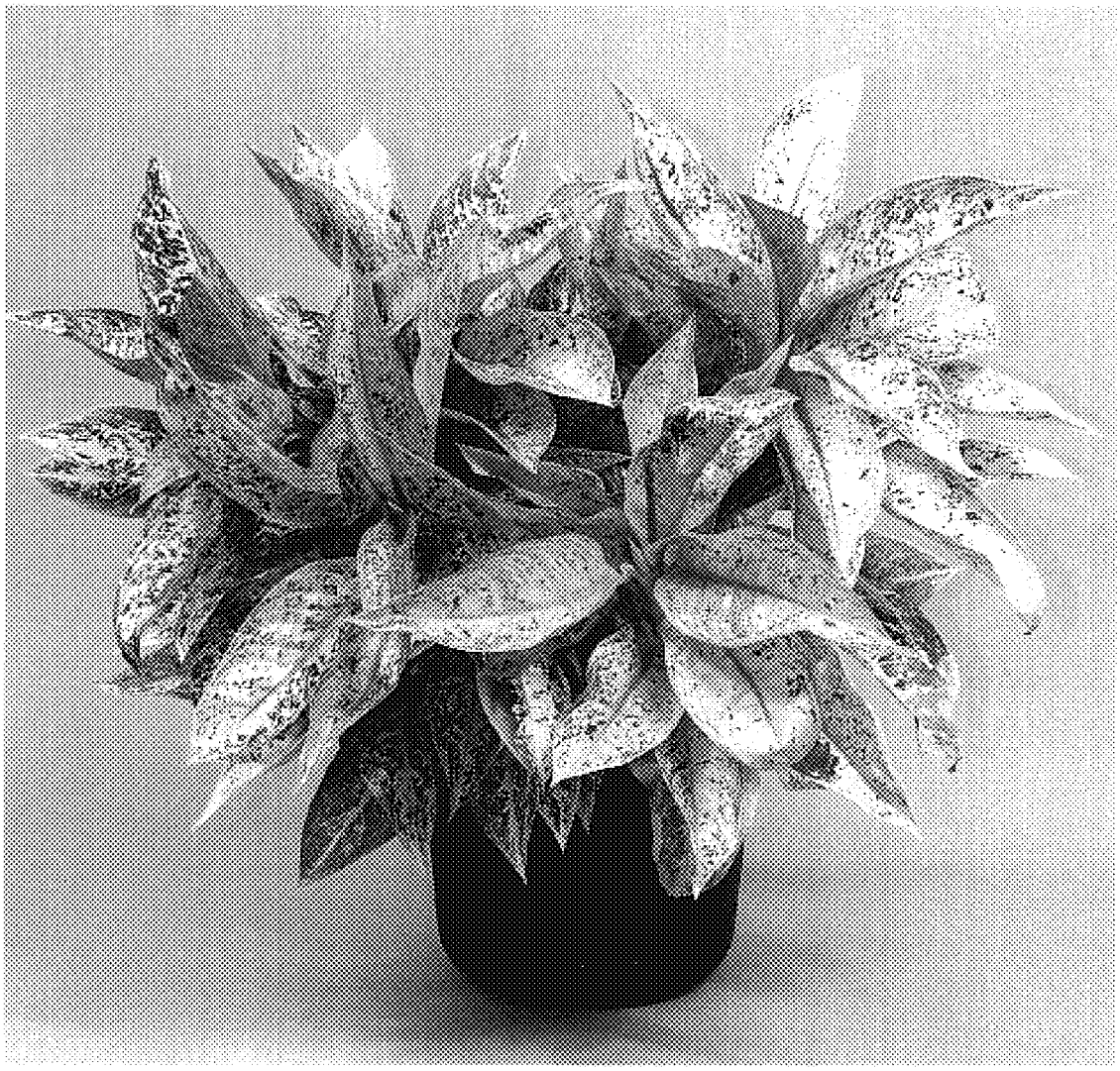
FIG. 1 shows the overall plant habit of the plant.
Figure 2:
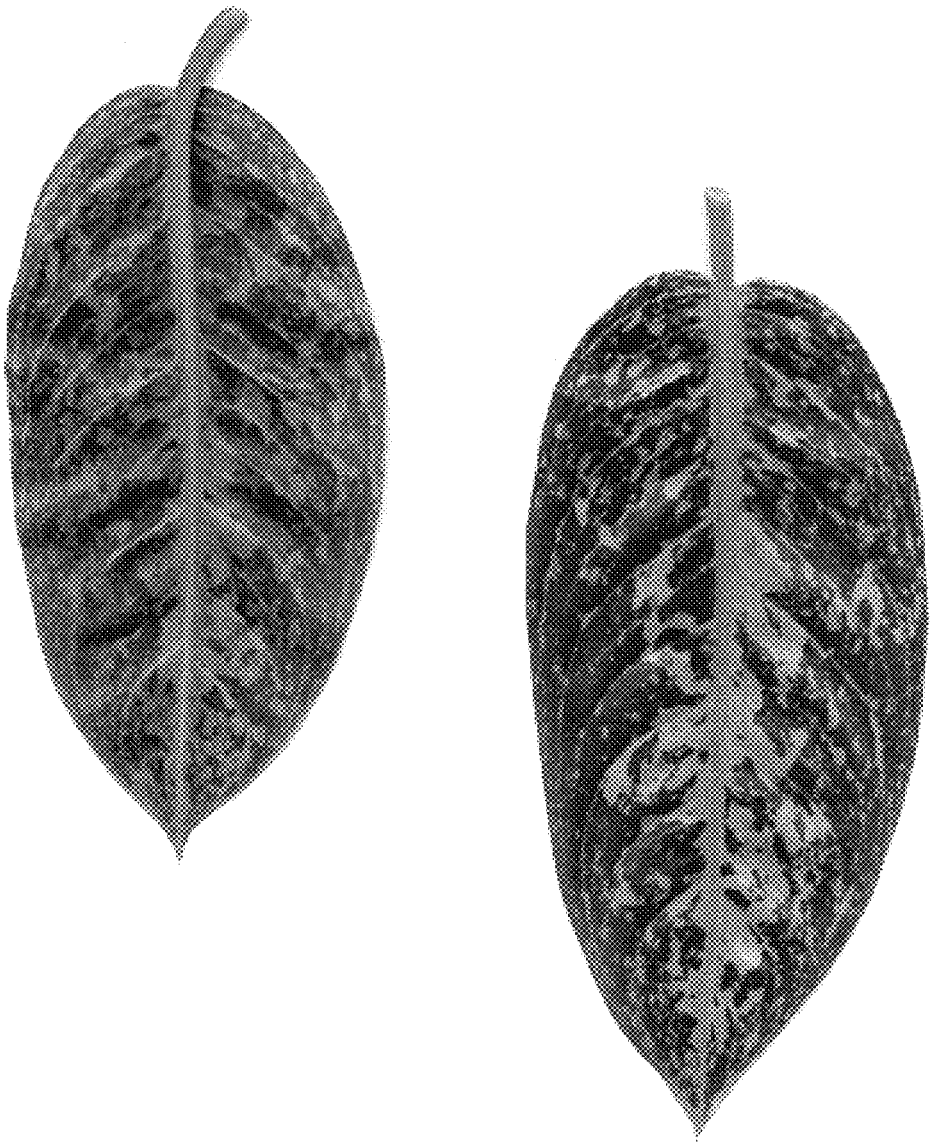
FIG. 2 shows the upper and lower surface of the mature leaves.

The following detailed description sets forth the distinctive characteristics of 'TWYAG021'. The data which define these characteristics were collected from asexual reproductions carried out in Apopka, Fla. The plant history was taken on 16-month old plants started from a single 4-leaf rooted cutting, still in a vegetative state and grown in Apopka, Fla. Rooted cuttings were planted in 20-cm pots and grown in a greenhouse in May 2006. The average daily temperature was about 85° to 95° F. and the average nightly temperature was about 65° to 78° F. The plants were pinched twice. Color readings were taken under natural light. Color references are primarily to the R.H.S. Colour Chart of The Royal Horticultural Society of London (R.H.S.) (2001).

DETAILED BOTANICAL DESCRIPTION

Classification:
*Family.*—Araceae
*Botanical.*—*Aglaonema commutatum* var. *tricolor×A. rotundum hybrida.*
*Common name.*—Chinese Evergreen.

Parentage: The female parent is an unknown individual plant of *A. commutatum* var. *tricolor* (patent status unknown) and the male parent is an unknown individual plant of *A. rotundum* (patent status unknown).

Growth:
*Form.*—Symmetrical; wider than tall; leaves lean outward.

*Growth and branching habit.*—Densely leafy, compact; upright branched growth habit with basal branching; small to intermediate in stature.

*Height* (*from soil to top of leaf plane*).—26 cm to 30 cm.

*Diameter* (*area of spread, measured from leaf tip to leaf tip across the canopy*).—46 cm to 53 cm.

*Time to produce a finished flowering plant.*—16-months starting from a single 4-leaf rooted cutting and pinched twice.

*Growth rated.*—Typical of commercial *Aglaonema* cultivars.

*Vigor.*—Vigorous; plants produce numerous axillary branches and leaves.

*Root description.*—Abundant, fleshy white roots with finer lateral branches.

*Number of divisions or clumps per year.*—About 4 to 7, 4-leaf cuttings per year.

*Durability of foliage to stresses.*—Leaves hold up well against damage from shipping and handling; plant is durable, excellent indoor keeping quality.

*High temperature tolerance.*—To about 104° F. for several hours without damage.

*Low temperature tolerance.*—To about 55° F., for several hours without damage.

Stems:

*Number of branches per plant.*—12.

*Length* (*from soil line to the junction of the newest two leaves*).—13 cm.

*Diameter* (*measured from the midpoint*).—1.1 cm.

*Internode length.*—1.2 cm to 2.1 cm.

*Color.*—Immature: RHS 146C and faintly mottled with RHS 144A. Mature: Between RHS 160C to RHS 157B, mottled with RHS 146B. Oldest stems: RHS 148D marbled with colors between RHS 147A. to RHS 147B.

*Appearance* (*shape*).—Columnar, cylindrical upright.

*Aspect.*—Vertical, upright.

*Strength.*—Sturdy, strong, somewhat flexible.

*Axillary buds.*—Shape: Elliptic, flat. Length: 0.4 cm. Width: 0.25 cm. Color: RHS 155C tinged with RHS 146C.

Leaves:

*Arrangement.*—Alternate, single, simple, arranged in a spiral along the stem.

*Quantity of leaves per stem.*—7.

*Immature leaf* (*new expanded leaf*).—Color: Upper surface: Base color is between RHS 147A to RHS 146A with spots and mottling between RHS 145C to RHS 145D and often tinged with RHS 182D (pink); areas adjacent to the midrib and primary veins are prominently marked with colors between RHS 182D to RHS 63C, with highlights of RHS 53C. Lower surface: Between RHS 147B to RHS 146C to RHS 146B base color with spots and mottling of between RHS 145C to RHS 145D and often flushed with RHS 50C (pink); areas adjacent to the primary veins and midrib marked with RHS 50C.

*mature leaf.*—Color: Upper surface: Base color darker than but closest to RHS 147A covered with spots and flecks between RHS 145C to RHS 145D and often tinged with RHS 182D (pink); areas adjacent to the primary veins and midrib are prominently marked with colors between RHS 63C to RHS 63D with highlights of RHS 53C. Lower surface: Base color is between RHS 147A to RHS 147B with spots and mottling of RHS 50C (pink); areas adjacent to the primary veins and midrib marked with RHS 50C; entire lower surface often tinged with RHS 50C.

*Length.*—14.0 cm to 16.5 cm.

*Width.*—General: The leaf blade folds upward along the midrib. Flattened: 6.0 cm to 9.5 cm. Not flattened: 4.0 cm to 6.5 cm.

*Shape.*—Ovate to elliptic.

*Apex.*—Acute to acuminate.

*Base.*—Obtuse.

*Margin.*—Smooth, entire, mostly flat with some broad undulations.

*Appearance* (*on both surfaces.*—).—Smooth; immature leaves shiny; mature leaves glossy; the leaf blade is convex between the main veins resulting in a textured appearance.

*Pubescence* (*for both surfaces*).—Absent.

*Venation pattern.*—Pinnate.

*Venation color* (*Immature leaf*).—Upper surface: Primary veins: Between RHS 182D to RHS 63C Midrib: Between RHS 182D to RHS 63C with highlights of RHS 53C and streaks of RHS 146B (green). Lower surface: Primary veins: Between RHS 50C to RHS 50D Midrib: RHS 50C.

*Venation color* (*Mature leaf*).—Upper surface: Primary veins: Between RHS 63C to RHS 63D with highlights of RHS 53C. Midrib: Between RHS 63C to RHS 63D with highlights of RHS 53C and streaks of RHS 146B (green). Lower surface: Primary veins: RHS 50C Midrib: RHS 50C; proximally is darker and between RHS 53C to RHS 53D.

*Petioles.*—Aspect: Vertical upright when newly expanded, becoming curved outward and about 45° with maturity Length: 8.5 cm Diameter: Distal: 0.4 cm Proximal (petiole and petiole sheath clasps the stem proximally): Flattened: 2.5 cm Natural diameter: 1.1 cm Color: Distal: Between RHS 53C to RHS 53D (between the top of the wing and the base of the leaf) Proximal: Between RHS 53D to RHS 50C to RHS 50D often streaked or mottled with RHS 146A (green) Area adjacent to stem: RHS 155D. Wing length: 5.4 cm. Wing diameter: Mid-point: 0.9 cm Base: 1.1 cm Depth: 0.6 cm Wing color: Inside: RHS N155C tinged with RHS 63C (pink); areas of RHS146A (green) on the outside is visible through the inside. Outside: Between RHS 53D to RHS 50C to RHS 50D often mottled or streaked with RHS 146A (green) Area adjacent to stem: RHS 155D.

Inflorescence: None observed.

Fruit and Seed Set: None observed.

Disease and insect resistance: Typical of *Aglaonema;* no particular susceptibility or resistance to pests or diseases noted.

COMPARISON WITH PARENTAL AND COMMERCIAL CULTIVARS

'TWYAG0021' differs from the female parent an unknown individual plant of *A. commutatum* var. tricolor in that 'TWYAG0021' has leaves with an upper surface of pinkish-white and green, while the female parent has leaves with an upper surface of plain green with silver stripes. The petioles of 'TWYAG0021' are dark-pink, while the female parent has petioles that are light-pink. In addition, 'TYWAG0021' has profuse suckering, while the female parent has moderate suckering.

'TWYAG0021' differs from the male parent an unknown individual plant of *A. rotundum* in that 'TWYAG0021' has leaves with a lower surface color of pinkish tinted green, while the male parent has a dark-purple or maroon color on the lower surface of the leaves. 'TWYAG0021' has pink veins, while the male parent has red veins. In addition, 'TWYAG0021' has ovate to elliptic leaves, while the male parent has ovate leaves.

'TWYAG0021' differs from the commercial variety 'Red Gold' (unpatented) in that 'TWYAG0021' has a pinkish tinted green color on the lower surface of the leaves, while 'Red Gold' has a pale yellowish green color on the lower surface of the leaves. 'TWYAG0021' has profuse suckering, while 'Red Gold' has moderate suckering. In addition, 'TWYAG0021' has ovate to elliptic leaves, while 'Red Gold' has ovate elliptic to broadly elliptic leaves.

I claim:

1. A new and distinct cultivar of *Aglaonema* plant as shown and described herein.

* * * * *